United States Patent
Fukada et al.

(10) Patent No.: US 9,857,350 B2
(45) Date of Patent: *Jan. 2, 2018

(54) COAL-TO-COAL ADHESIVENESS EVALUATION METHOD

(71) Applicant: JFE STEEL CORPORATION, Chiyoda-ku, Tokyo (JP)

(72) Inventors: Kiyoshi Fukada, Tokyo (JP); Hiroyuki Sumi, Tokyo (JP); Hidekazu Fujimoto, Tokyo (JP); Izumi Shimoyama, Tokyo (JP); Takashi Anyashiki, Tokyo (JP); Tetsuya Yamamoto, Tokyo (JP); Yusuke Dohi, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 512 days.

This patent is subject to a terminal disclaimer.

(21) Appl. No.: 14/387,729

(22) PCT Filed: Mar. 25, 2013

(86) PCT No.: PCT/JP2013/001979
§ 371 (c)(1),
(2) Date: Sep. 24, 2014

(87) PCT Pub. No.: WO2013/145677
PCT Pub. Date: Oct. 3, 2013

(65) Prior Publication Data
US 2015/0039242 A1    Feb. 5, 2015

(30) Foreign Application Priority Data
Mar. 27, 2012 (JP) ................. 2012-071518

(51) Int. Cl.
*G06F 19/00* (2011.01)
*G01N 33/22* (2006.01)
(Continued)

(52) U.S. Cl.
CPC .......... *G01N 33/222* (2013.01); *C10B 57/04* (2013.01); *G01N 2013/0283* (2013.01)

(58) Field of Classification Search
USPC .............................................. 702/19, 22, 30
See application file for complete search history.

(56) References Cited

FOREIGN PATENT DOCUMENTS

| JP | 8-176553 A | 7/1996 |
|---|---|---|
| JP | 2005-281355 A | 10/2005 |

OTHER PUBLICATIONS

D.R. Absolom et al.: "Surface Properties of Coal Particles in Aqueous Media II. Adhesion of Coal Particles to Polymeric Substrates", Colloids and Surfaces, vol. 17, No. 2, Feb. 1, 1986, pp. 143-157.

(Continued)

*Primary Examiner* — Lam Nguyen
(74) *Attorney, Agent, or Firm* — RatnerPrestia

(57) ABSTRACT

In order to evaluate the compatibility of coals used in coke production and to produce cokes with desired strength by blending coals in consideration of the compatibility, the invention provides a technique which evaluates the adhesion strength obtained when two kinds of coals are carbonized based on properties of the coals. Surface tensions of two kinds of semicokes obtained by heat treating two kinds of coals are measured. Based on the difference between the two measured values of surface tension, the quality of the adhesiveness between the two kinds of coals is evaluated.

6 Claims, 2 Drawing Sheets

(51) Int. Cl.
*C10B 57/04* (2006.01)
*G01N 13/02* (2006.01)

(56) References Cited

OTHER PUBLICATIONS

Supplementary European Search Report dated Feb. 27, 2015, application No. EP 13 76 8941.
International Search Report dated May 28, 2013, application No. PCT/JP2013/001979.
Miyazu, Okuyama, Suzuki, Fukuyama and Mori, Nippon Kokan Gihou (Nippon Kokan Technical Report), vol. 67, p. 1 (1975).
Sakamoto and Igawa, CAMP-ISIJ, vol. 11, p. 689 (1998).
Toshihiro Aramaki et al., Journal of the Fuel Society of Japan, vol. 69 (1990), p. 355.
Toshihiro Aramaki et al., Journal of the Fuel Society of Japan, vol. 70 (1991), p. 525.
Japanese Office Action/Notice of Allowance in JP Appln. No. JP2014-507418 with partial English language translation, dated Jun. 17, 2014, 4 pages.

COAL-TO-COAL ADHESIVENESS EVALUATION METHOD

CROSS REFERENCE TO RELATED APPLICATIONS

This is the U.S. National Phase application of PCT/JP2013/001979, filed Mar. 25, 2013, which claims priority to Japanese Patent Application No. 2012-071518, filed Mar. 27, 2012, the disclosures of each of these applications being incorporated herein by reference in their entireties for all purposes.

FIELD OF THE INVENTION

The present invention relates to a method for evaluating coal-to-coal adhesiveness to produce a high-strength coke in carbonizing a coal blend including two kinds of coals.

BACKGROUND OF THE INVENTION

Cokes are used as blast-furnace raw materials to produce hot metal. High strength cokes are desirable because otherwise the cokes are disintegrated in the blast furnace to deteriorate gas permeability in the blast furnace and to destabilize the production of hot metal.

When metallurgical coke is produced by carbonizing coals in a horizontal chamber coke oven, the strength of the metallurgical coke is variable depending on factors such as the selection of raw material coals, preparation methods, carbonization conditions, quenching conditions and post-treatment conditions. Of these factors, the conditions associated with the facility and the operation conditions are facility restrictions and thus cannot be easily altered to a great degree. Thus, the selection of raw material coals is considered as the most important factor for controlling coke properties.

Various coal blending methods for obtaining cokes having desired strength are known in the art, and one such method is mentioned in Non Patent Literature 1. All these methods determine suitable blending by predicting the strength of coke produced based on the properties of raw material coals that are blended.

However, such known methods are at times incapable of accurately predicting the coke strength. One possible reason is a phenomenon called the "compatibility of coals". Non Patent Literature 2 mentions that there is often no additivity between the strengths of cokes obtained from individual brands of coals that are to be blended together, and the strength of a coke obtained from a coal blend including a plurality of brands with different properties. The "compatibility of coals" may be represented by the difference between a theoretical sum and a measured value of coke strength. When the measured value is larger than the theoretical sum, the compatibility is "good". The compatibility is "bad" when the measured value is smaller than the theoretical sum. Various studies have been carried out to determine the cause that gives rise to the "compatibility" effect. However, no techniques have been established that evaluate the "compatibility of coals" and specify a combination of good compatible coals.

The compatibility of coals is probably affected by variable adhesion strengths between different kinds of coals, and various techniques have been studied for the evaluation of adhesive strength at interfaces of different kinds of coals. For example, interface contacts between various combinations of different coals are observed and classified into four contact conditions, namely, diffusive contact, non-diffusive contact, fissile contact and porous contact. Based on the assumption that these conditions are brought about by the caking properties of coals and also by micro fissures generated by shrinkage when the coals are melted by heating and then become solidified, the adhesiveness is evaluated based on the maximum fluidity obtained by the Gieseler plastometer method that is a caking index, and on the solidification temperature. (See Non Patent Literatures 3 and 4.)

Non Patent Literature

NPL 1: Miyazu, Okuyama, Suzuki, Fukuyama and Mori, Nippon Kokan Gihou (Nippon Kokan Technical Report), Vol. 67, p. 1 (1975)

NPL 2: Sakamoto and Igawa, CAMP-ISIJ, Vol. 11, p. 689 (1998)

NPL 3: Toshihiro Aramaki et al., Journal of the Fuel Society of Japan, Vol. 69 (1990), p. 355

NPL 4: Toshihiro Aramaki et al., Journal of the Fuel Society of Japan, Vol. 70 (1991), p. 525

SUMMARY OF THE INVENTION

As described above, there is a lot of uncertainty about the compatibility of coals and difficulties remain in evaluating the adhesive strength that will be obtained when two kinds of coals are carbonized in contact with each other or in predicting the strength of the obtainable coke. For example, the method of Non Patent Literature 2 is complicated due to the fact that the strength estimation requires the actual implementation of a blending test. Non Patent Literatures 3 and 4 associate the contact conditions with the maximum fluidity obtained by the Gieseler plastometer method and the solidification temperature. However, the relationship between these properties and the adhesion strength is not clear and thus the disclosed methods are little more than evaluations involving strength estimation models.

In view of the current techniques for the evaluation of adhesion strength, it is an object of the present invention to provide a technique for evaluating the adhesion strength obtained when two kinds of coals are carbonized based on properties of the coals, thereby the compatibility of coals used in coke production is evaluated and the coals are blended in consideration of the compatibility so that the coke attains desired strength.

A summary of the present invention that achieves the above object includes the following.

[1] A coal-to-coal adhesiveness evaluation method for evaluating an adhesiveness between two kinds of coals that are to be carbonized in contact with each other, the method comprising: evaluating the adhesiveness based on a difference between surface tensions of two kinds of semicokes obtained by heat treating the two kinds of coals.

[2] The coal-to-coal adhesiveness evaluation method described in [1], further comprising: evaluating the coal-to-coal adhesiveness as poor when the difference between the two measured values of surface tension is a prescribed threshold or more.

[3] A coal-to-coal adhesiveness evaluation method for evaluating the adhesiveness between two kinds of coals that are to be carbonized in contact with each other, the method comprising: evaluating the adhesiveness based on a value of interfacial tension between two kinds of semicokes obtained by heat treating the two kinds of coals.

[4] The coal-to-coal adhesiveness evaluation method described in [3], wherein the value of interfacial tension is calculated from measured values of surface tension of the two kinds of semicokes.

[5] The coal-to-coal adhesiveness evaluation method described in [4], wherein the value of interfacial tension is calculated according to Equation (3) below:
[Math. 3]

$$\gamma_{AB} = \gamma_A + \gamma_B - 2\varphi\sqrt{\gamma_A\gamma_B} \quad (3)$$

wherein $\gamma_A$: the surface tension of semicoke A that is one of the two kinds of semicokes, $\gamma_B$: the surface tension of semicoke B that is the other of the semicokes, $\gamma_{AB}$: the interfacial tension between the two kinds of semicokes A and B, and $\varphi$: an interaction parameter.

[6] The coal-to-coal adhesiveness evaluation method described in [4], wherein the value of interfacial tension is calculated according to Equation (9) below:
[Math. 4]

$$\gamma_{AB} = \gamma_A + \gamma_B - 2\exp[-\beta(\gamma_A - \gamma_B)^2]\sqrt{\gamma_A\gamma_B} \quad (9)$$

wherein $\gamma_A$: the surface tension of semicoke A that is one of the two kinds of semicokes, $\gamma_B$: the surface tension of semicoke B that is the other of the semicokes, $\gamma_{AB}$: the interfacial tension between the two kinds of semicokes A and B, and $\beta$: a constant.

[7] The coal-to-coal adhesiveness evaluation method described in any one of [3] to [6], wherein the method evaluates the coal-to-coal adhesiveness as poor when the value of interfacial tension is a prescribed threshold or more.

[8] The coal-to-coal adhesiveness evaluation method described in any one of [1] to [7], wherein the surface tension is measured by a film flotation method.

According to the present invention, the quality of the adhesiveness at an interface between different types of coals for coke production can be evaluated based on the surface tensions or the interfacial tension of semicokes obtained by heat treating the coals in contact with each other. The evaluation results allow for the selection of a combination of well compatible coals that are used as raw materials for coke production. By the selection of coals based on the evaluation, cokes having high strength may be produced.

According to the present invention, the coal-to-coal adhesiveness (the quality of the compatibility of coals) can be evaluated based on properties of coals, such evaluation being impossible by the conventional methods. Thus, coals that are to be purchased or sold can be effectively selected. For example, a coal II may be selectively purchased or sold with certainty that this coal exhibits good compatibility with a coal I which is a currently used brand and will make a good blend with the coal I to give a raw material for high-strength coke. Further, the present invention allows one who has selected one of the coals to be supplied, namely, a coal I, to identify with certainty that a coal II exhibits good compatibility with the coal I and thereby to determine to supply the coal I in combination with the coal II.

DETAILED DESCRIPTION OF EMBODIMENTS OF THE INVENTION

Figure 1:
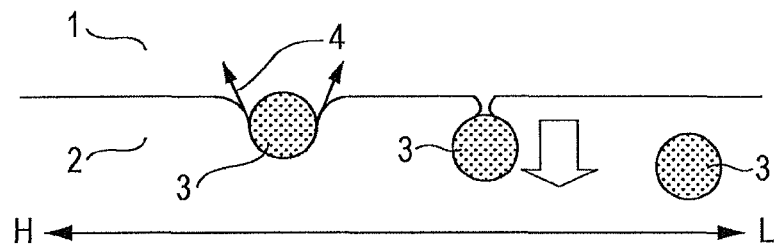
FIG. 1 is a view illustrating the principle of the measurement of surface tension by a film flotation method.

First, the present inventors have found that when two kinds of coals are carbonized, the coal-to-coal adhesiveness can be evaluated through the steps described below. The present invention assumes that two kinds of coals are carbonized, in detail, a coal blend including two kinds of coals is carbonized to produce a coke.

Step 1: Obtain measured values of surface tension of two kinds of heat treated products obtained by heat treating two kinds of coals. Here, the measured values of surface tension may be obtained by actually measuring the surface tension with respect to the two kinds of heat treated products, or may be provided by a third party.

Step 2: Evaluate the quality of adhesiveness between the two kinds of coals based on the difference between the two measured values of surface tension.

Also, the present inventors focused on the following: the difference between measured values of surface tension between two kinds of semicokes has a certain relationship with the interfacial tension between the semicokes. The present inventors have further found that the quality of adhesiveness between two kinds of coals may be evaluated based on the interfacial tension between the two kinds of semicokes.

Next, the aforementioned steps and the findings according to the present invention will be described in detail. It is generally known that the strength of a contact between two kinds of substances having different surface tensions is increased as the difference between the surface tensions is smaller. When coals are carbonized into cokes, the coals are first melted by heating and are then solidified to produce cokes. In this process, the different kinds of coals are bonded together to form a strong coke structure. It has been considered that this bonded structure is formed by the fusion bonding of coals in which the fusibility of coals (for example, the Gieseler maximum fluidity MF) serves an important role. In contrast to this concept, the present inventors have focused on the phenomenon itself in which different kinds of coals are bonded together and have reasoned that the strength of this bonding would affect in some way the strength of cokes. The present inventors have then studied the bonding phenomenon and have experimentally identified that the difference in surface tension is related with the strength of cokes.

It is considered desirable that the values of surface tension used in the study of the bonding phenomenon be surface tensions of plastic coals measured at temperatures (350 to 800° C.) where coals actually start to be softened and melted and the plastic coals are bonded together and solidified to the completion of coking. The reason for this is because the adhesion strength between coals is probably affected by the surface tensions of softened and plastic coals that are exhibited during the time in which the coals start to be softened and melted and become solidified to the completion of coking. Accordingly, it will be preferable that the surface tensions of coals that are of interest in the study of adhesion strength be measured in the above temperature range.

However, no methods are known that can measure the surface tensions of substances at such high temperatures. The present inventors then studied various alternative methods. As a result, the present inventors have found that the adhesion strength between coals can be well represented by the surface tensions of coals that have been heat treated and cooled to room temperature or, preferably, the surface tensions of products obtained by heat treatment and rapid cooling of coals, and have also found that this bonding phenomenon also affects coke strength. These heat-treated products of coals are called semicokes. Preferably, the semicokes are heat-treated products of coals that are obtained by heating the coals to temperatures of 350 to 800° C. where the coals start to be softened and melted and the plastic coals are bonded together and solidified to the completion of coking, and then cooling the heated products.

[Step 1 in Evaluation of Coal-to-Coal Adhesiveness: Measurement of Surface Tensions]

Examples of the surface tension measurement methods that are known include a sessile drop method, a capillary-rise method, a maximum bubble pressure method, a drop weight method, a pendant drop method, a ring method, a Wilhelmy method, an advancing/receding contact angle method and a tilting plate method. Coal is composed of various molecular structures and the surface tension thereof is expected to be nonuniform. Thus, it is particularly preferable to use a method capable of evaluating a surface tension distribution, for example, a film flotation method (see D. W. Fuerstenau, International Journal of Mineral Processing, 20, p. 153 (1987)). This method determines a distribution of surface tension with respect to a finely crushed substance as a sample, and is similarly applicable to semicoke obtained by heat treatment of coal.

The basic principle of a film flotation method will be described with reference to FIG. 1. A film flotation method is a technique based on the concept that when a crushed sample particle 3 is caused to fall from a gas phase 1 onto the surface of a liquid 2 and when the sample particle 3 is about to sink in the liquid 2 (the sample particle 3 that has sunk is illustrated in the middle of FIG. 1 as having a contact angle of almost 0°), the surface tension of the sample particle 3 is equal to that of the liquid 2. Arrows 4 in FIG. 1 indicate the surface tension of the sample particle 3. The white arrow in the middle of FIG. 1 indicates the direction of sinking, and the horizontal arrows mean that the surface tension of the liquid is higher on the left side (H) and is lower on the right side (L). Sample particles were dropped onto liquids having various surface tensions, and the mass percentages of the sample particles that floated on the liquids were obtained. The results were plotted on a frequency distribution curve to give a surface tension distribution illustrated in FIG. 2.

Exemplary indicators for surface tension include an average value of a surface tension distribution, a standard deviation of a surface tension distribution, a value of surface tension at the peak top of a surface tension distribution, the maximum surface tension and the minimum surface tension in a surface tension distribution, and a distribution function of a surface tension distribution. An average value of a surface tension distribution ($\bar{\gamma}$ with an overline) is represented by the following equation.

[Math. 1]

$$\bar{\gamma} = \int \gamma f(\gamma) d\gamma \quad (1)$$

In Equation (1), γ: the surface tension and f(γ): the frequency in the surface tension distribution.

A standard deviation ($\sigma_\gamma$) of a surface tension distribution is represented by the following equation.

[Math. 2]

$$\sigma_\gamma = [\int (\gamma - \bar{\gamma})^2 f(\gamma) d\gamma]^{0.5} \quad (2)$$

Figure 2:
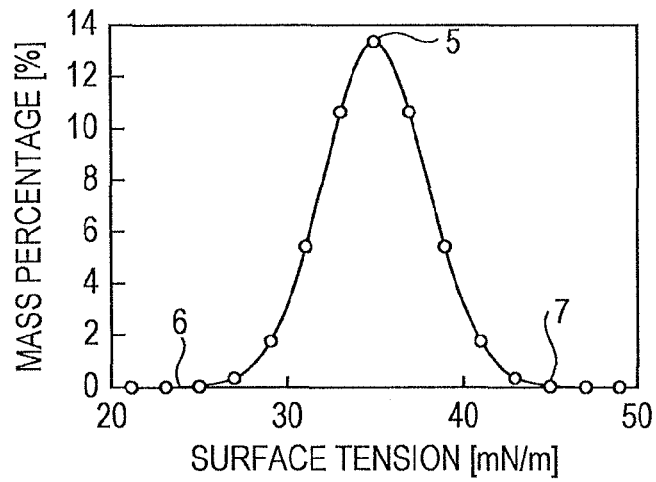
FIG. 2 is a graph illustrating a distribution of surface tension on a frequency distribution curve.

The frequency distribution curve of surface tension illustrated in FIG. 2 shows a peak value 5 in the surface tension distribution, a minimum surface tension 6 in the surface tension distribution, and a maximum surface tension 7 in the surface tension distribution. Examples of the distribution functions of surface tension include distributions similar to the surface tension distribution in shape, such as normal distribution, logarithmic normal distribution, F-distribution, chi-square distribution, exponential distribution, gamma distribution and beta distribution. The average value of a surface tension distribution obtained may be used as a representative value of the surface tension of the sample. In consideration of the distribution, for example, the maximum surface tension in the surface tension distribution may be used as a representative value of surface tension.

In the use of heat-treated coals (semicokes) as samples, the heat treatment temperature is preferably set to a range of temperatures at which the samples are softened and melted. Specifically, the softening temperature range is appropriately the temperature range of 350 to 800° C. Temperatures which particularly contribute to bonding are probably the temperatures at which the samples are in the softened and molten state, namely, 350 to 550° C., and the contact structures are probably determined at temperatures near 500° C. Thus, the heating temperature is particularly preferably in the vicinity of 500° C., for example, 480 to 520° C.

In the present invention, it is preferable that the samples used in the film flotation method be heat-treated products (semicokes) obtained by heating (carbonizing) coals in the absence of air or in the presence of an inert gas at 350° C. or above followed by cooling. The measurement of surface tension of coals is possible by the film flotation method, and the surface tensions of coals are correlated with coke strength and thus may be used to estimate the coke strength. However, the surface tensions of semicokes are more strongly correlated with coke strength than the surface tensions of coals. Thus, the estimation of coke strength desirably involves the surface tensions of semicokes rather than the surface tensions of coals.

The reason why the coals are cooled in an inert gas is for the purpose of reducing errors in the measurement of surface tensions. Coals immediately after being heated are very hot. If such coals are cooled in an oxygen-containing atmosphere, the surface is partially oxidized to cause structural changes and the values obtained by the surface tension measurement will contain errors. Examples of the inert atmospheres include rare gas atmospheres such as of helium or argon gas, and nitrogen gas atmosphere. Nitrogen gas is usually used.

In an embodiment of the present invention, specifically, coals are heat treated through the following steps.

(a) Coals are crushed. Desirably, coals are crushed to particle sizes of 250 μm or less in accordance with the proximate analysis of coal described in JIS M8812 in order to prepare homogeneous samples from coals having non-uniform structures and properties. Particularly preferably, coals are crushed to finer sizes of 200 μm or less.

(b) The coals crushed in the step (a) are heated at an appropriate heating rate in the absence of air or in an inert gas. The coals may be appropriately heated to a temperature in the aforementioned range of 350 to 800° C. Most preferably, the heating rate is determined in accordance with the heating rate that will be used when the coke under the evaluation by interfacial tension is produced.

(c) The coals heated in the step (b) are cooled. In this cooling, it is preferable that the coals be rapidly cooled in the manner described above.

There will be described an example of the above heat treatment steps and the preparation of samples for the measurement of surface tension that is performed after the heat treatment.

Step 1. Coals are crushed to particle sizes of 200 μm or less, and the crushed coals are heated to 500° C. at 3° C./min in an inert gas atmosphere (carbonization step). The heating rate is set at 3° C./min because the heating rate in the production of cokes in a coke oven is approximately 3° C./min.

Step 2. The coals are cooled in an inert gas atmosphere (cooling step), and are thereafter crushed to 150 μm or less.

Step 3. The crushed coals are dried at 120° C. for 2 hours in a stream of dry inert gas (drying step). The drying methods are not particularly limited as long as water attached on the surface may be removed. For example, the coals may be heated at 100 to 200° C. in an inert gas such as nitrogen or argon, may be vacuum dried, or may be dried under reduced pressure. The dry inert gas may be obtained by passing the gas through a layer packed with a desiccant such as silica gel.

Semicokes obtained by heat treating coals through the steps 1 to 3 may be used as samples for the measurement of surface tension. The reasons why the above steps are performed will be described below.

If coals are used as the samples in a film flotation method, the carbonization step 1 (heating to 500° C.) is omitted and the coals are subjected to the sample crushing in the step 2 and to the drying step 3. The thus-treated coals are used as the samples in a film flotation method.

The surface tension that is directly obtained by a film flotation method is critical surface tension (liquid surface tension when the contact angle is 0°). First, surface tensions of substances A and B different from each other will be described. Based on the Girifalco-Good equation, the following relationship is held between the interfacial tension between the substances A and B, and the surface tensions of the substances A and B.

[Math. 3]

$$\gamma_{AB} = \gamma_A - \gamma_B - 2\varphi\sqrt{\gamma_A \gamma_B} \quad (3)$$

In Equation (3), $\gamma_A$ and $\gamma_B$: the surface tensions of the substances A and B, $\gamma_{AB}$: the interfacial tension between the substances A and B, and $\varphi$: an interaction parameter. The interaction parameter $\varphi$ may be obtained by experiment and is known to be varied depending on the substances A and B. From Equation (3), the following relationship is held between the surface tension $\gamma_S$ of the solid (coal or semicoke) and the surface tension $\gamma_L$ of the liquid, and the interfacial tension $\gamma_{SL}$ between the liquid and the solid.

$$\gamma_{SL} = \gamma_S + \gamma_L - 2\varphi(\gamma_S \gamma_L)^{0.5} \quad (4)$$

From the Young's equation, the following relationship is held between the surface tension $\gamma_S$ of the solid (coal or semicoke) and the surface tension $\gamma_L$ of the liquid, and the interfacial tension $\gamma_{SL}$ between the liquid and the solid.

$$\gamma_S = \gamma_L \cos\theta + \gamma_{SL} \quad (5)$$

Here, $\theta$: the contact angle of the solid (coal) to the liquid.

Equations (4) and (5) lead to the following relational expression.

$$1 + \cos\theta = 2\varphi(\gamma_S/\gamma_L)^{0.5} \quad (6)$$

By substituting $\theta=0°$ and $\gamma_L = \gamma_C$ ($\gamma_C$: critical surface tension) into Equation (6), the following relational expression may be derived.

$$1 + 1 = 2\varphi(\gamma_S/\gamma_C)^{0.5} \quad (7)$$

Squaring both sides of Equation (7) results in the following relationship between the surface tension $\gamma_S$ of the solid (coal or semicoke) and the critical surface tension $\gamma_C$.

$$\varphi^2 \gamma_S = \gamma_C \quad (8)$$

Based on Equation (8), the surface tension $\gamma_S$ of the coal may be determined from the critical surface tension $\gamma_C$ and the interaction parameter $\varphi$.

There is a significant difference in structure between the liquid and the coal or the semicoke used in the film flotation method. Compared to this difference, the difference present between the coals (the types of coals) will be smaller. The interaction parameter $\varphi$ is a coefficient (a constant) that represents an influence produced by the respective molecular structures. Provided that this interaction parameter $\varphi$ is constant irrespective of the brands of coals, the surface tension $\gamma_S$ of the solid (coal or semicoke) may be represented by the critical surface tension $\gamma_C$ alone. Accordingly, it can be said that the surface tension of coal or semicoke may be evaluated with the critical surface tension alone.

Because the values of surface tension of coals or plastic coals are distributed in the range of 20 to 73 mN/m, the film flotation method appropriately involves a liquid that has a surface tension in this range. For example, a liquid having a surface tension of 20 to 73 mN/m may be prepared from an aqueous solution of an organic solvent such as ethanol, methanol, propanol, tert-butanol or acetone. Based on the principle of the measurement, the surface tension is desirably measured when the contact angle is substantially 0°. Because the contact angle is increased with increasing particle size of the crushed sample particles, the samples used in the measurement of surface tension preferably have smaller particle sizes. However, sample particles having a particle size of less than 53 μm are prone to be aggregated. In view of these facts, the sample particles are preferably crushed to a particle size of 53 to 150 μm.

Because the film flotation method utilizes a phenomenon in which substances (sample particles) float due to their surface tension, it is necessary that the measurement be performed under conditions where the gravity applied to the substances is negligible. If the substances have a high density, the contact angle is disadvantageously increased by the influence of gravity. It is therefore desirable that the sample substances have a density of 2000 kg/m³ or less at which the gravity will not probably affect the contact angle. Various types of coals and semicokes satisfy this condition, and powders of any types of coals and semicokes such as hard coking coals, non- or slightly caking coals and anthracites may be used as the sample particles in the film flotation method to measure the surface tensions. Further, pitch, oil coke, coke breeze, dust, waste plastics and additives such as biomass may be similarly tested.

Coals, or semicokes obtained from the coals may be tested in the above manner to measure their surface tensions.

[Step 2 in Evaluation of Coal-to-Coal Adhesiveness: Evaluation of Level of Adhesiveness]

The two semicokes that are obtained from the two kinds of coals used as raw materials for coke production are tested by the aforementioned method to determine beforehand values of surface tension of (the respective types of) the semicokes. In the case where a mixed coal that is a mixture of several kinds of coals is used as a raw material for coke production, the surface tension may be measured actually with respect to a semicoke obtained by heat treating the mixed coal. Alternatively, the surface tensions may be measured with respect to the respective semicokes obtained from individual coals that constitute the mixed coal and the weighted average of the surface tensions may be obtained by weighting the mixing proportions of the coals, thereby determining the surface tension of a semicoke that will be obtained by heat treating the mixed coal. In the evaluation of the compatibility between two kinds of coals, a difference is obtained between the measured values of surface tension of the respective semicokes and the compatibility is evaluated (judged) to be poor when the difference is large and is evaluated to be good when the difference is small.

Studies with respect to various blends have confirmed that the strength of the obtainable coke is significantly lowered in all cases where the difference between the surface tensions of the semicokes is 1.5 [mN/m] or more. Accordingly, this value may be used as the prescribed threshold in determining whether or not the adhesiveness between two kinds of coals is good. If the difference between the surface tensions of the semicokes is 1.5 or more, the coal-to-coal adhesiveness is evaluated as poor with reliability. For good comparison of the measured values of surface tension of the semicokes, the surface tensions of the semicokes are most preferably obtained by heat treatment at the same heat treatment temperature. It is, however, possible to compare average values of surface tension of semicokes obtained by heat treatment at a certain temperature range. Further, the measured values compared to each other may be surface tensions of semicokes obtained by heat treating individual coals at respective softening and melting characteristic temperatures (for example, the maximum fluidity temperatures, the softening onset temperatures or the resolidification temperatures).

The above quantitative evaluation of the compatibility of coals makes it possible to select compatible coal brands. Carbonizing a coal blend including coals selected in this manner results in a coke that achieves higher strength than obtained when a coke is produced from a coal blend prepared without any consideration of compatibility.

[Evaluation of Coal-to-Coal Adhesiveness Based on Value of Interfacial Tension Between Two Kinds of Coals]

The aforementioned difference in surface tension also has an influence on the interfacial tension at a contact interface. That is, the adhesion strength at an interface between two kinds of substances is quantitatively affected by the interfacial tension between the substances. In other words, the higher the interfacial tension, the lower the adhesion strength. Thus, a value of interfacial tension may be used instead of the difference in surface tension. The interfacial tension between two kinds of substances may be measured directly, or may be estimated based on values of surface tension of the respective substances by a known method. In addition to obtaining the difference in surface tension, a value of interfacial tension may be obtained based on a higher-accuracy estimation theory and the compatibility may be evaluated similarly as described above with use of the obtained interfacial tension.

As mentioned hereinabove, the interfacial tension between substances A and B different from each other may be obtained from the surface tensions of the substances A and B according to Equation (3).

[Math. 3]

$$\gamma_{AB}=\gamma_A+\gamma_B-2\varphi\sqrt{\gamma_A\gamma_B} \tag{3}$$

D. Li, and A. W. Neumann et al. assumed that the interaction parameter $\varphi$ in Equation (3) would be increased with increasing difference between the surface tensions $\gamma_A$ and $\gamma_B$ of the substances A and B, and have extended Equation (3) and proposed the following equation.

[Math. 4]

$$\gamma_{AB}=\gamma_A+\gamma_B-2\exp[-\beta(\gamma_A-\gamma_B)^2]\sqrt{\gamma_A\gamma_B} \tag{9}$$

In Equation (9), $\beta$: a constant. The constant $\beta$ is a value derived by experiment, and D. Li, and A. W. Neumann et al. have calculated it to be 0.0001247 $(m^2/mJ)^2$ (see J. K. Spelt and D. Li, "The equation of state approach to interfacial tensions, in Applied Surface Thermodynamics", A. W. Neumann and J. K. Spelt (Eds), Advances in Chemistry Series, vol. 63, Marcel Dekker, New York, 1996, pp. 239-292). Thus, it can be said that the interfacial tension between substances A and B may be derived by measuring the surface tensions of the substances A and B and substituting the measured values of surface tension into Equation (3) or Equation (9). The use of Equation (3) requires the implementation of an experiment to obtain a value of $\varphi$. Thus, the use of Equation (9) which assumes a value of $\varphi$ is more desirable in order to facilitate the derivation of interfacial tension.

Studies have confirmed that the strength of the obtainable coke is significantly lowered in all cases where the value of interfacial tension obtained by the above method according to Equation (3) or Equation (9) is 0.03 [mN/m] or more, the value corresponding to a difference between the surface tensions of the semicokes of 1.5 [mN/m]. Accordingly, 0.03 [mN/m] may be used as the threshold interfacial tension in the case where the quality of the adhesiveness between two kinds of coals is evaluated based on a value of interfacial tension. Provided that the substances A and B in Equation (3) or Equation (9) are semicoke A and semicoke B, $\gamma_A$ and $\gamma_B$ in Equation (3) or Equation (9) are the surface tension of the semicoke A and the surface tension of the semicoke B, respectively, and $\gamma_{AB}$ is the interfacial tension between the two semicokes A and B.

While the above embodiments describe the application of the present invention to coals that represent the major proportion of raw materials for cokes, the present invention may be applied in principle to other raw materials that are blended such as oil cokes, pitches and other organic substances.

The evaluation of the compatibility of coals for coke production in the above manner realizes judgments described below. In the purchase of coals, for example, a coal brand may be purchased selectively which is expected to exhibit good compatibility with a currently used coal brand and thus to give a coke having high strength. In the selling of coals, on the other hand, coal dealers can sell appropriate coals to customers usually using brands which have good compatibility with the coals and can thereby allow the customers to produce high-strength cokes in their plants. In the use of coals, well compatible coals (having as similar surface tensions as possible) may be combined so as to produce cokes having high strength.

While the conventional methods are incapable of evaluating the adhesion strength between coals based on properties of the coals, the inventive methods allow for such evaluation based on values of surface tension of semicokes. Thus, the present invention makes it possible to effectively select coals in the selling, the purchase and the use of coals.

Example 1

The surface tensions of semicokes obtained by heat treating various coals (types or brands) were measured by a film flotation method. Based on the results, coal blends including two kinds of coals were prepared and carbonized to produce cokes. The strength of these cokes was measured to study the relationship between the difference between the surface tensions of the semicokes, and the coke strength. Table 1 describes the coals used.

TABLE 1

| Coals | Ro [%] | logMF [log ddpm] | γ [mN/m] |
|---|---|---|---|
| Coal A | 0.71 | 1.32 | 40.2 |
| Coal B | 0.72 | 2.11 | 40.9 |
| Coal C | 0.75 | 2.28 | 40.9 |
| Coal D | 0.99 | 3.08 | 41.6 |
| Coal E | 1.00 | 2.43 | 39.6 |
| Coal F | 1.03 | 2.15 | 40.1 |
| Coal G | 1.07 | 2.09 | 38.9 |
| Coal H | 1.26 | 0.95 | 40.5 |
| Coal I | 1.62 | 1.28 | 37.8 |

The coals in Table 1 were tested to determine conventional coal property parameters, namely, the mean maximum reflectance of vitrinite (Ro, in accordance with JIS M 8816), the common logarithm value of maximum fluidity MF obtained by the Gieseler plastometer method (log MF, in accordance with JIS M 8801), and the surface tension (γ) by a film flotation method.

Samples for the measurement of surface tension by a film flotation method were prepared by the following steps.

Step 1. The coals were crushed to particle sizes of 200 μm or less and were heated to 500° C. at 3° C./rain.

Step 2. The coals were cooled in a nitrogen atmosphere and were thereafter crushed to 150 μm or less.

Step 3. The crushed coals were dried at 120° C. for 2 hours in a stream of dry nitrogen.

The semicokes obtained by the steps 1 to 3 were used as samples. The measurement of surface tension by a film flotation method involved an aqueous ethanol solution that was inexpensive and easy to handle. From the surface tension distribution obtained, the average value of the surface tension distribution was derived using Equation (1). This average value of the surface tension distribution served as the measured value of surface tension (γ) of the coal. Table 1 describes the mean maximum vitrinite reflectance values Ro [%] and the common logarithm values of Gieseler maximum fluidity log MF [log ddpm] of the coals, and the measured values of surface tension γ [mN/m] of semicokes obtained from the respective coals.

From the coals described in Table 1, two kinds of coals were selected and the adhesion strength between the two selected coals was measured. The combinations of the selected coals are described in Table 2.

TABLE 2

| Combinations of coals | Adhesion strength [MPa] | Average logMF [log ddpm] | Δγ [mN/m] | γinter [mN/m] |
|---|---|---|---|---|
| A-G | 64 | 1.70 | 1.3 | 0.027 |
| A-I | 37 | 1.30 | 2.4 | 0.093 |
| B-E | 135 | 2.27 | 1.3 | 0.027 |
| B-I | 35 | 1.70 | 3.1 | 0.155 |
| C-E | 125 | 2.36 | 1.3 | 0.027 |
| D-H | 174 | 2.18 | 1.1 | 0.020 |
| E-F | 144 | 2.29 | 0.5 | 0.004 |
| E-G | 88 | 2.26 | 0.7 | 0.008 |
| E-I | 57 | 1.86 | 1.8 | 0.052 |
| G-I | 68 | 1.68 | 1.1 | 0.019 |

The adhesion strength between the two kinds of coals described in Table 2 was measured as follows.

1. The two coals were thoroughly mixed with each other in a mass ratio of 1:1, and the mixed coal was crushed to 70 μm or less.

2. The amount of the coal was adjusted such that the size of a coal tablet would be 6.6 mm in diameter and 2.5 mm in thickness, and the coal was placed into a mold having a hole 6.6 mm in diameter.

3. A load of 14 MPa was applied to the mold for 10 seconds to prepare the coal tablet. Ten such coal tablets were prepared for each coal blend.

The bulk densities of the coal tablets were different from brand to brand and were in the range of from 860 to 920 kg/m$^3$. The ten coal tablets were arranged on a packed layer of coke breeze adjusted to sizes of 1 mm or less and were carbonized. The coke breeze had been packed in an iron container 200 mm×200 mm×H 500 mm. The carbonization conditions were such that the coal tablets were carbonized by being heated in a nitrogen atmosphere to 1000° C. at 3° C./min and the carbonized coal tablets were cooled in a nitrogen atmosphere. The compressive strength was measured with use of an autograph manufactured by Shimadzu. The measurement sample was compressed in the thickness direction and the load at breakage was measured. The load was divided by the area of the surface of the measurement sample that had been subjected to the load, thereby obtaining the pressure as the adhesion strength. The compressive strength and the area of the loaded surface were measured with respect to the ten measurement samples for each coal blend, and the average of the adhesion strengths was obtained as the adhesion strength of the coal blend. The results of the measurement of adhesion strength are described in Table 2. Table 2 also describes average log MF calculated by averaging the log MF values of the two kinds of coals.

Because the coal blends used in the test of adhesion strength included two kinds of coals, the samples contained a large number of interfaces formed between the coals. The compressive strength reflects not only the adhesion strength at such interfaces but also the strengths of cokes obtained from the individual coals and also the adhesion strength of coal particles of the same brand. Based on the facts that the coals had been finely crushed to increase the number of interfaces and that ½ of the points of contacts between the coal particles would stochastically form interfaces between different kinds of coals, the obtained adhesion strength is considered to reflect the interface adhesiveness.

Figure 3:
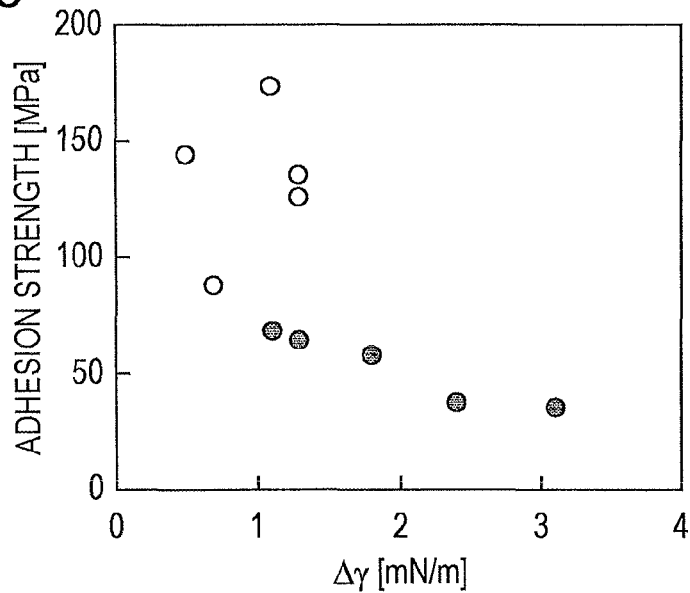
FIG. 3 is a graph illustrating a relationship between the difference in surface tension and the adhesion strength.

FIG. 3 is a graph illustrating a relationship between the difference in surface tension (Δγ) [mN/m] of coals and the adhesion strength [MPa]. In the graph, the black dots indicate the adhesion strengths of combinations of coals with an average log MF of less than 2 and the white dots indicate the adhesion strengths of combinations of coals with an average log MF of 2 or more. Further, Table 2 describes differences in surface tension between the coals, Δγ [mN/m]. As illustrated in FIG. 3, the strength was increased and higher adhesiveness between the two coals was obtained as the difference in surface tension Δγ between the two semicokes was smaller, and the combinations of coals with a large difference in surface tension were demonstrated to have poor adhesiveness. In particular, a marked relationship has been illustrated in which the combinations of coals having an average log MF of less than 2 achieved higher adhesion strength with decreasing difference between the surface tensions. Coal blends having a small value of average log MF tend to form cokes in such a manner that the melts of the coals simply contact with each other rather than that the melts of the coals are mixed with each other and form a mixed interface. This is probably the reason why the relationship between the difference in surface tension and the adhesion strength tends to be more marked.

As described in the item of $\Delta\gamma$ in Table 2 and as illustrated in FIG. 3, the strength of the obtainable coke is significantly decreased in all cases where $\Delta\gamma$ is 1.5 [mN/m] or more. When $\Delta\gamma$ is 1.3 [mN/m] or less, a considerable number of the combinations of coals achieve an improvement in adhesion strength. The combinations of coals achieve high adhesion strength in all cases where $\Delta\gamma$ is 1.1 [mN/m] or less. Thus, the threshold of $\Delta\gamma$ in determining the quality of the adhesiveness between two kinds of coals is preferably 1.5 [mN/m], more preferably 1.3 [mN/m], and most preferably 1.1 [mN/m].

Figure 4:
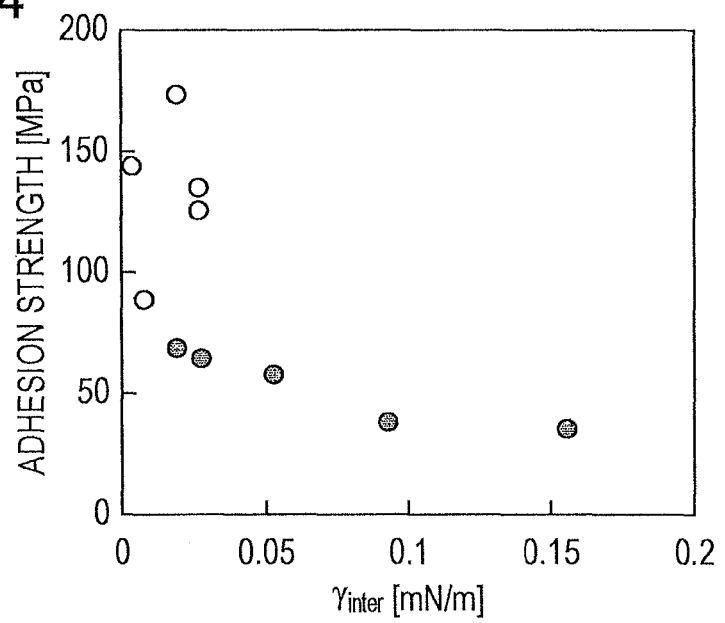
FIG. 4 is a graph illustrating a relationship between the interfacial tension (γinter) calculated from surface tensions, and the adhesion strength.

FIG. 4 is a graph illustrating a relationship between the interfacial tension calculated from the two measured values of surface tension according to Equation (9), and the adhesion strength. In this graph, similarly to FIG. 3, the black dots and the white dots indicate adhesion strengths. The fact that the interfacial tension is increased as the difference in surface tension is larger confirms that FIG. 4 illustrates a tendency similar to that shown in FIG. 3.

As described in the item of $\gamma_{inter}$ in Table 2 and as illustrated in FIG. 4, the strength of the obtainable coke is significantly decreased in all cases where $\gamma_{inter}$ is 0.03 [mN/m] or more. When $\gamma_{inter}$ is 0.027 [mN/m] or less, chances are markedly increased for the combinations of coals to achieve an improvement in adhesion strength. The combinations of coals achieve high adhesion strength in all cases where $\gamma_{inter}$ is 0.020 [mN/m] or less. Thus, the threshold of $\gamma_{inter}$ in determining the quality of the adhesiveness between two kinds of coals is preferably 0.03 [mN/m], more preferably 0.027 [mN/m], and most preferably 0.020 [mN/m].

The above studies have confirmed that there is a correlation between the difference between the surface tensions of two kinds of semicokes obtained by heat treating two kinds of coals, or the interfacial tension between such semicokes, and the strength (the adhesion strength) of the coke obtained from a coal blend including the two kinds of coals. Consequently, it has been confirmed that the adhesiveness between two kinds of coals may be evaluated based on the difference in surface tension or the interfacial tension.

Example 2

Next, studies were performed to examine the influence on coke strength of the difference between the surface tensions of semicokes or the interfacial tension between semicokes. In general, it is known that the strength of a coke obtained by carbonizing a coal mixture or a coal blend in a coke oven is affected by the Ro and the log MF of the coal blend as well as by the adhesion strength (for example, Non Patent Literature 1). Thus, the influence of surface tension on coke strength cannot be studied by actually carbonizing the coal blends described in Table 2 because the coal blends in Table 2 have various Ro and log MF and the influence of such factors is not negligible.

In order to clarify how the coke strength is affected by the difference in surface tension or the interfacial tension, the influence of the difference in surface tension or the interfacial tension is desirably studied under conditions where the average Ro and the average log MF of the coal blends are identical. In such studies in which, for example, a comparison is made between a combination of coal X and coal Y1 and a combination of coal X and coal Y2, it is necessary that Y1 and Y2 have the same Ro and the same log MF and the surface tensions of semicokes obtained therefrom be different. The Ro and the log MF of the coal blends have to be adjusted in the preferred ranges in order to produce cokes qualifying for the evaluation. Thus, the selection of coals used in the test is very limited.

Thus, the present inventors prepared three types of mixed coals A, B and C whose Ro and log MF were identical and surface tensions $\gamma$ were different, by mixing five to eight kinds of coals selected from coals having Ro of 0.71 to 1.62 [%], log MF of 0.95 to 4.43 [log ddpm] and surface tension $\gamma$ of 37.2 to 41.6 [mN/m] as measured in the form of a semicoke by the method described in EXAMPLE 1. Next, 30% [dry basis mass %] of coal J and 70% [dry basis mass %] of one of the mixed coals A, B and C were mixed with each other to prepare coal blends a, b and c. The properties of the coal J and the mixed coals A, B and C are described in Table 3.

TABLE 3

| Coals | Ro [%] | logMF [log ddpm] | $\gamma$ [mN/m] | Coal blend a | Coal blend b | Coal blend c |
|---|---|---|---|---|---|---|
| Coal J | 1.15 | 1.49 | 37.6 | 30 | 30 | 30 |
| Mixed coal A | 0.96 | 2.81 | 38.9 | 70 | 0 | 0 |
| Mixed coal B | 0.96 | 2.81 | 39.7 | 0 | 70 | 0 |
| Mixed coal C | 0.96 | 2.81 | 40.4 | 0 | 0 | 70 |
| Difference between surface tensions $\Delta\gamma$ of semicokes obtained from coal J and mixed coal [mN/m] | | | | 1.3 | 2.1 | 2.8 |
| Interfacial tension $\gamma_{inter}$ between semicokes obtained from coal J and mixed coal [mN/m] | | | | 0.029 | 0.049 | 0.077 |
| Coke strength DI 150/15 [—] | | | | 83.1 | 81.4 | 80.4 |
| Coke strength CSR [%] | | | | 55.5 | 50.9 | 48.1 |

Here, the Ro and the log MF of the mixed coals are values obtained by averaging Ro values and log MF values of individual coal brands used in the mixture while weighting the mixing proportions of the coals. The surface tensions $\gamma$ are values actually measured with respect to the respective mixed coals by the method described in EXAMPLE 1.

The coal blend weighing 16 kg was conditioned such that 100 mass % of the particles had a size of 3 mm or less and the water content was 8 mass %. The coal blend was then loaded into a can to a bulk density of 750 kg/m³ and was carbonized in an electric furnace. The carbonization was performed at a furnace wall temperature of 1100° C. for 6 hours. The product was cooled with nitrogen, thereby producing coke. The strength of the coke produced was evaluated in terms of drum index DI 150/15 based on a drum strength measurement method in accordance with JIS K2151 and also in terms of coke strength after $CO_2$ reaction, CSR, in accordance with ISO 18894. Table 3 describes the results of the measurement of coke strength.

From Table 3, it has been demonstrated that the strength of the coke obtained was increased as the difference in surface tension Δγ between the semicokes obtained from the two kinds of coals was smaller or as the interfacial tension γinter between the semicokes was smaller. These results show that the method for the evaluation of adhesiveness between two kinds of coals is applicable also to the prediction of coke strength. Accordingly, the evaluations of adhesiveness according to the present invention include the evaluation of coke strength.

Example 3

Coal K and coal L were heat treated by the same method as in EXAMPLE 1 while changing the heat treatment temperature, and the surface tensions of the obtained semicokes were measured. The results are described in Table 4.

TABLE 4

| | Heat treatment temperature (° C.) | | | | | |
|---|---|---|---|---|---|---|
| | 350 | 400 | 450 | 500 | 600 | 800 |
| Surface tension of semicoke of coal K [mN/m] | 31.9 | 33.0 | 35.5 | 41.1 | 45.2 | 52.3 |
| Surface tension of semicoke of coal L [mN/m] | 29.8 | 30.4 | 32.4 | 37.6 | 42.2 | 48.7 |

From Table 4, the surface tension tends to be increased as the heat treatment temperature is higher in the temperature range of 350° C. and above. On the other hand, the difference between the surface tensions of the two kinds of semicokes treated at the same heat treatment temperature is substantially constant. Thus, the inventive method is effective when the temperature of the heat treatment for the preparation of semicokes is preferably in the range of 350° C. to 800° C. When the coal-to-coal adhesiveness is evaluated based on the surface tensions of two kinds of semicokes, it is necessary that the samples to be evaluated be prepared at substantially the same heat treatment temperature.

EXPLANATION OF REFERENCE NUMERALS

1 GAS PHASE
2 LIQUID
3 SAMPLE PARTICLE
4 SURFACE TENSION
5 PEAK VALUE IN SURFACE TENSION DISTRIBUTION
6 MINIMUM SURFACE TENSION IN SURFACE TENSION DISTRIBUTION
7 MAXIMUM SURFACE TENSION IN SURFACE TENSION DISTRIBUTION

The invention claimed is:

1. A coal-to-coal adhesiveness evaluation method for evaluating an adhesiveness between first and second kinds of coals that are to be carbonized in contact with each other, the method comprising:

evaluating the adhesiveness based on a value of interfacial tension between first and second kinds of semicokes obtained by heat treating the first and second kinds of coals in a temperature range of between 350° C. and 800° C., wherein the value of interfacial tension is calculated according to Equation (3) below from measured values of surface tension of the first and second kinds of semicokes:

[Math. 3]

$$\gamma_{AB} = \gamma_A + \gamma_B - 2\varphi\sqrt{\gamma_A\gamma_B} \qquad (3)$$

wherein
$\gamma_A$: the surface tension of the first kind of semicokes,
$\gamma_B$: the surface tension of the second kind of semicokes,
$\gamma_{AB}$: the interfacial tension between the first and second kinds of semicokes, and
$\varphi$: an interaction parameter.

2. The coal-to-coal adhesiveness evaluation method according to claim 1, further comprising: evaluating coal-to-coal adhesiveness as poor when the value of interfacial tension is a prescribed threshold or more.

3. The coal-to-coal adhesiveness evaluation method according to claim 1, wherein the surface tensions of the first and second kinds of semicokes are measured by a film flotation method.

4. A coal-to-coal adhesiveness evaluation method for evaluating an adhesiveness between first and second kinds of coals that are to be carbonized in contact with each other, the method comprising:

evaluating the adhesiveness based on a value of interfacial tension between first and second kinds of semicokes obtained by heat treating the first and second kinds of coals in a temperature range of between 350° C. and 800° C., wherein the value of interfacial tension is calculated according to Equation (9) below from measured values of surface tension of the first and second kinds of semicokes:

[Math. 4]

$$\gamma_{AB} = \gamma_A + \gamma_B - 2\exp[-\beta(\gamma_A-\gamma_B)^2]\sqrt{\gamma_A\gamma_B} \qquad (9)$$

wherein
$\gamma_A$: the surface tension of the first kind of semicokes,
$\gamma_B$: the surface tension of the second kind of semicokes,
$\gamma_{AB}$: the interfacial tension between the first and second kinds of semicokes, and
$\beta$: a constant.

5. The coal-to-coal adhesiveness evaluation method according to claim 4, further comprising: evaluating the coal-to-coal adhesiveness as poor when the value of interfacial tension is a prescribed threshold or more.

6. The coal-to-coal adhesiveness evaluation method according to claim 4, wherein the surface tensions of the first and second kinds of semicokes are measured by a film flotation method.

* * * * *